United States Patent [19]

Guglielmetti

[11] Patent Number: 4,719,051

[45] Date of Patent: Jan. 12, 1988

[54] PROCESS FOR THE PREPARATION OF 4,4'-DINITROSTILBENE-2,2'-DISULFONIC ACID AND ITS SALTS

[75] Inventor: Leonardo Guglielmetti, Bottmingen, Switzerland

[73] Assignee: Ciba-Geigy Corporation, Ardsley, N.Y.

[21] Appl. No.: 896,561

[22] Filed: Aug. 13, 1986

Related U.S. Application Data

[63] Continuation of Ser. No. 782,617, Oct. 1, 1985, abandoned, which is a continuation of Ser. No. 699,496, Feb. 8, 1985, abandoned, which is a continuation of Ser. No. 294,954, Aug. 21, 1981, abandoned, which is a continuation of Ser. No. 154,338, May 29, 1980, abandoned.

[30] Foreign Application Priority Data

Jun. 8, 1979 [CH] Switzerland .................... 5369/79

[51] Int. Cl.⁴ .......................................... C07C 143/24
[52] U.S. Cl. .................................................. 260/505 R
[58] Field of Search ...................................... 260/505 R

[56] References Cited

U.S. PATENT DOCUMENTS 2,212,084 8/1940 Straub et al. .
2,821,550 1/1958 Strobel .

OTHER PUBLICATIONS

Journal of Organic Chem., vol. 32, pp. 137–146 (Jan., 1967).
Chemical Abstracts, vol. 83, 1975.
Chemical Abstract, vol. 84, 1976.
Miyata et al., Chem Abst., vol. 83, 113377k (1975).
Kompolshy et al., Chem Abst., vol. 84, 58886u (1976).
Glen A. Russell et al.; J. Am. Chem. Soc., vol. 84, pp. 4153–4154 (1962).
Glen A. Russell et al.,—J. Am. Chem. Soc., vol. 88, pp. 5491–5497 (1966).
Glen A. Russell et al.; J. Am. Chem. Soc., vol. 89, pp. 300–308, (1967).
Glen A. Russell et al.; J. Org. Chem., vol. 32, pp. 137–146 (1967).

*Primary Examiner*—Alan Siegel
*Attorney, Agent, or Firm*—Edward McC. Roberts; Meredith C. Findlay

[57] ABSTRACT

A process for the preparation of 4,4'-dinitrostilbene-2,2'-disulfonic acid and its salts, of the formula

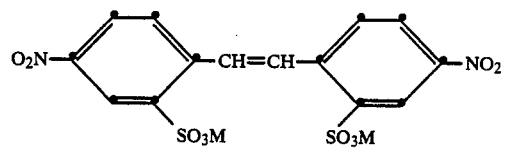

in which M is hydrogen or an alkali metal cation, by oxidation of 4-nitrotoluene-2-sulfonic acid in organic solvents, and also the reduction of the resulting acid or salt, without isolation, to give 4,4'-diamino- or (4-amino-4'-nitro)-stilbene-2,2'-disulfonic acid or salts thereof.

15 Claims, No Drawings

PROCESS FOR THE PREPARATION OF 4,4'-DINITROSTILBENE-2,2'-DISULFONIC ACID AND ITS SALTS

This application is a continuation of application Ser. No. 782,617, filed Oct. 1, 1985, which is a continuation of Ser. No. 699,496, filed Feb. 8, 1985, which is a continuation of Ser. No. 294,954, filed Aug. 21, 1981 which is a continuation of Ser. No. 154,338, filed May 29, 1980, all abandoned.

The present invention relates to a process for the preparation of 4,4'-dinitrostilbene-2,2'-disulfonic acid and its salts.

The processes for the industrial preparation of 4,4'-dinitrostilbene-2,2'-disulfonic acid and its salts are generally known and comprise oxidative condensation of 2 mols of 4-nitrotoluene-2-sulfonic acid under aqueous alkaline conditions. Oxidising agents which have been described are oxygen (air) in the presence of a catalyst or sodium hypochlorite (cf., for example, A. G. Green and A. R. Wahl, B. 30, 3097–3101 (1897); 31, 1079 (1898); German Reichspatent No. 106,961; C. 1900 I, 1085; German Reichspatent No. 113,514 and C. 1900 II, 703). However, despite modern technical improvements, these processes yield 4,4'-dinitrostilbene-2,2'-disulfonic acid and its salts only in relatively poor yields which are between 60 and 75% (cf., for example, German Offenlegungsschrift No. 2,258,530).

In the past 15 years numerous efforts have been made to improve the yield from this condensation reaction using physico-chemical, mathematical and analytical methods and also computer models. However, these efforts remained without success [cf., for example, C.A. 83, 113,377h (1975); C.A. 85, 192,288z, 192,289a, 192,290n (1976); C.A. 86, 16029c (1977); Chimie Analytique 50, 251–254 (1968) and Chimie et Industrie, Genie Chimique 101, 1439–1447 (1969)].

The use of aqueous sodium hypochlorite solutions as the oxidising agent is associated with numerous disadvantages. The oxidation proceeds very rapidly and must therefore also be carried out very rapidly if the yield is not to be adversely affected by the formation of coloured by-products. Since, however, the oxidation also proceeds as a highly exothermic reaction, heat removal problems also have to be solved. Moreover, large amounts of liquid have to be transported, processed and stored, and the activity of these liquids changes continuously depending on the temperature, the structural material of the storage vessels and small amounts of impurities which are always present in aqueous sodium hypochlorite solutions. This instability is particularly pronounced in the warm seasons of the year. In addition, the large amounts of NaCl which are continuously present in the aqueous sodium hypochlorite solutions have adverse effects from the ecological and economic points of view. Thus, because of the restriction on the permissible concentration of intermediates and by-products formed during the oxidation, the oxidation can be carried out only with very dilute solutions, as a result of which the productivity is adversely affected.

The use of oxygen or air as the oxidising agent is associated with numerous other disadvantages. The oxidation proceeds very slowly and for this reason very long circulation times are required, even in the presence of catalysts. The productivity is thus adversely affected. During the oxidation, the reaction solution must continuously be saturated with oxygen, so that the yield is not adversely affected by the formation of coloured by-products [cf. Chimie et Industrie, Genie Chimique 101, 1439–1447 (1969)].

All of the oxidative condensations of 4-nitrotoluene-2-sulfonic acid to 4,4'-dinitrostilbene-2,2'-disulfonic acid, and its salts, which have hitherto been disclosed in the literature have been carried out using aqueous systems only.

However, it has been disclosed in the literature that nitro-, dinitro- and trinitro-toluenes can be oxidised, in organic solvents, in the presence of strong bases and in the presence or absence of catalysts, by oxygen (air) to give complex mixtures of products which contain corresponding nitrostilbene compounds [cf. C.A. 84, 58,886n (1976); Acta Chem. Scand. 25, 3509–3516 (1971); J. Org. Chem. 32, 137–46 (1967); and Advan. Chem. Ser. 51, 112–71 (1965)].

However, these oxidation reactions proceed with poor yields of nitrostilbene compounds and are always accompanied by the formation of considerable amounts of by-products.

It has now been found, surprisingly, that 4,4'-dinitrostilbene-2,2'-disulfonic acid and its salts can be prepared in high yields, and avoiding the disadvantages mentioned above, by oxidation of 4-nitrotoluene-2-sulfonic acid if the oxidation is carried out in an organic solvent.

The process according to the invention for the preparation of 4,4'-dinitrostilbene-2,2'-disulfonic acid or its salts of the formula

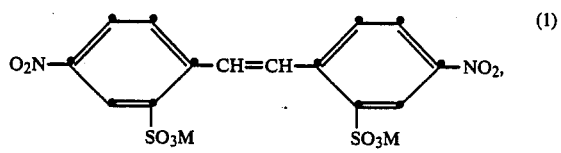

in which M is hydrogen or an alkali metal ion, by oxidation of 4-nitrotoluene-2-sulfonic acid comprises carrying out the oxidation in organic solvents.

The oxidation according to the invention is preferably carried out in the presence of strong bases and in the presence or absence of catalysts.

Alkali metal ions M are in particular sodium ions and potassium ions.

4-Nitrotoluene-2-sulfonic acid, which is used as the starting material, is a known compound which is prepared very easily by sulfonation of 4-nitrotoluene.

Suitable organic solvents are in particular those in which 4-nitrotoluene-2-sulfonic acid and the strong bases have adequate solubility, for example aprotic dipolar solvents of the general formula

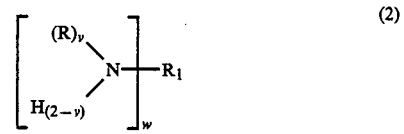

in which R is a lower alkyl group having 1 to 4 carbon atoms, $R_1$ is the radical of a low-molecular carboxylic acid having 1 to 4 carbon atoms—especially formic acid and acetic acid—or the phosphoric acid radical, w is the basicity of the acid and the v's are the numbers 0, 1 or 2; cyclic amides, such as N-methyl-2-pyrrolidone, N-acetyl-2-pyrrolidone and N-methyl-ε-caprolactam; amides of carbonic acid, such as tetramethylurea and dimorpholinocarbonyl; amides of phosphorus acid, of phosphoric acid, of phenylphosphonic acid or of aliphatic phosphonic acids having 1 to 3 carbon atoms in the acid moiety, such as phosphoric acid triamide, phosphoric acid tris-(dimethylamide), phosphoric acid trimorpholide, phosphoric acid tripyrrolinide, phosphoric acid bis-(dimethylamide)morpholide, phosphorous acid tris-(dimethylamide) and the tetramethyldiamide of methanephosphonic acid; amides of sulfuric acid and of aliphatic or aromatic sulfonic acids, such as tetramethylsulfamide, the dimethylamide of methanesulfonic acid or p-toluenesulfonamide; sulfur-containing solvents, such as organic sulfones and sulfoxides, for example dimethylsulfoxide and sulfolane; and aliphatic and aromatic nitriles, 3-alkoxypropionitriles, aliphatic ketones, alkyl esters and alkoxyalkyl esters of aliphatic monocarboxylic acids, cyclic ethers, dialkyl ethers, N,N-disubstituted amides of aliphatic monocarboxylic acids, ethylene glycol dialkyl ethers and diethylene glycol dialkyl ethers.

The solvents can be used on their own or as solvent mixtures.

Particularly important solvents are, however, the aprotic dipolar solvents which have the general formula (2). Preferred compounds of the general formula (2) are those in which v is 2. Amongst these compounds, dimethylformamide, hexamethylphosphoric acid triamide, diethylformamide, dimethylacetamide and diethylacetamide are of particular interest. The use of mixtures of one or more such compounds with aliphatic low-molecular alcohols having 1 to 4 carbon atoms—especially methanol—has proved particularly advantageous.

The solvents used can be anhydrous, but do not have to be so. Small amounts of water such as occur in the industral solvents do not interfere in the oxidation.

Suitable strong bases are, in particular, the alkali metals or alkaline earth metals, the strongly basic compounds thereof and also strongly basic aluminium compounds, for example hydroxides, amides, hydrides, alcoholates and sulfides, and also strongly basic ion exchangers.

Alcoholates used are essentially those which are derived from open-chain, branched or cyclic lower aliphatic alcohols having 1 to 8 carbon atoms and preferably 1 to 4 carbon atoms. These alcoholates are preferably employed in the form of corresponding alcoholic solutions.

Preferably, the corresponding sodium compounds or potassium compounds are used, and the hydroxides, amides and alcoholates thereof are of particular importance in practice.

The strong bases mentioned are preferably used in the anhydrous state, either on their own or as a mixture. Small amounts of water such as arise in the technical-grade strong bases do not interfere in the oxidation.

The amount of base to be used varies within wide limits. Although the base is not consumed during the reaction and thus, per se, a catalytic amount would be sufficient, the base is, however, advantageously used in the equivalent amount and, moreover, is, however, also used in a multiple of the equivalent amount, the latter being the case especially when the reaction is carried out at temperatures at which some of the base is consumed by reaction with the solvent.

The optimum amount of base to be added can, however, be determined easily by preliminary experiments and is very frequently limited by the solubility of the base in the reaction solvent used.

Suitable catalysts are salts, oxides or hydroxides of heavy metal compounds and/or heavy metal-organic compounds, for example those of Co, Mn, Cr, Ce, Fe, Ni, Cu, Ru, Pd, Pt or Ir (cf., for example, Homogeneous Catalysis by Metal Complexes, Vol. I, Chapter 2: Activation of molecular oxygen, page 79, Academic Press New York and London 1974). Particularly important catalysts are, however, the salts, oxides or hydroxides of manganese and/or the manganese-organic compounds, for example manganese sulfate and/or manganese acetate.

Inorganic or organic bromine and/or iodine compounds, for example NaI, KI, KBr and ammonium bromide, can also advantageously be used.

Phase transfer catalysts can also advantageously be used, especially in those cases in which the strong bases to be used have an inadequate solubility in the solvent used.

Preferred salts are those of the formula

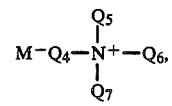

in which M is fluorine, bromine or iodine, or especially chlorine, $Q_4$ is hydrogen, alkyl having 1 to 18 carbon atoms, cyclohexyl, benzyl, phenyl or naphthyl and $Q_5$, $Q_6$ and $Q_7$ independently of one another are hydrogen or alkyl having 1 to 18 carbon atoms, and also N-alkyl-pyridinium halides having 1 to 18 carbon atoms in the alkyl moiety, especially the corresponding chlorides.

Examples of such salts are: ammonium chloride, ammonium bromide, methylamine hydrochloride, cyclohexylamine hydrochloride, aniline hydrochloride, dimethylamine hydrochloride, di-isobutylamine hydrochloride, triethylamine hydrochloride, triethylamine hydrobromide, tri-n-octylamine hydrochloride, benzyldimethylamine hydrochloride, tetramethylammonium chloride, bromide and iodide, tetraethylammonium chloride, bromide and iodide, tetra-n-propyl-ammonium chloride, bromide and iodide, tetra-n-butylammonium chloride, bromide and iodide, trimethyl-hexadecylammonium chloride, benzyldimethylhexadecylammonium chloride, benzyldimethyltetradecylammonium chloride, benzyltrimethyl-, -triethyl- and -tri-n-butyl-ammonium chloride, n-butyl-tri-n-propyl-ammonium bromide, octadecyltrimethylammonium bromide, phenyltrimethylammonium bromide or chloride and hexadecylpyridinium bromide and chloride.

The amount of catalyst used can vary within wide limits. In some cases it suffices if the catalyst is present in traces. In general, however, the catalyst is preferably used in an amount of about 0.1 to 15 percent by weight, based on the 4-nitrotoluene-2-sulfonic acid. The addition of open-chain or macrocyclic polyethers (crown ethers) is advantageous for a rapid course of reaction. Examples of such crown ethers are: 15-crown-5, 18-crown-6, dibenzo-18-crown-6, dicyclohexyl-18-crown-6 and 5,6,14,15-dibenzo-7,13-diaza-1,4-dioxa-cyclopentadeca-5,14-diene.

In general, the reaction temperature is not critical and can be between −20° C. and the boiling point of the solvent or solvent mixture, but it is preferably between −10° C. and 50° C. and in particular between 0° C. and 25° C.

Suitable oxidising agents are pure oxygen or mixtures thereof with inert gases, for example nitrogen and the like, and especially air, and the oxidation can be carried out at atmospheric pressure or under elevated pressure. Other oxidising agents, for example anhydrous hypochlorites or quinones, can also be employed in certain cases.

The oxidation according to the invention is very weakly exothermic and proceeds fairly rapidly, even at low temperatures, and without the formation of coloured by-products.

Due to the fact that coloured by-products are not formed, the 4,4'-dinitrostilbene-2,2'-disulfonic acid, and its salts, prepared according to the invention can, without isolation, be further reduced in a manner known per se to 4,4'-diaminostilbene-2,2'-disulfonic acid, which is an important intermediate for the preparation of dyes and fluorescent brightening agents, or be further reacted in a manner known per se in order to prepare dyes [cf. Kirk-Othmer, Encyclopaedia of Chemical Technology, 19, 1–14 (1969)].

The examples which follow illustrate the invention without implying any restriction. Percentages are by weight unless indicated otherwise.

EXAMPLE 1

50 ml of dimethylformamide are cooled to 0° C. and diluted, at this temperature, with stirring and cooling, with 108 g of a methanolic 30% sodium methylate solution. 1 g of manganese sulfate monohydrate is added to the resulting solution, and the solution is saturated with air at 0° C. by passing in a stream of dry air for 15 minutes at a rate of 5 l/hour, through a frit which dips into the solution.

A solution of 48 g of sodium 4-nitrotoluene-2-sulfonate of the formula

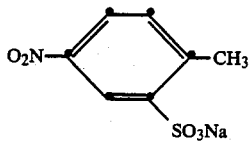

(100)

in 150 ml of dimethylformamide is added dropwise in the course of one hour to this solution at 0° to 5° C., with stirring, whilst continuing to pass in the stream of dry air at a rate of 5 l/hour, through the frit dipping into the solution. The reaction mixture, which during the addition of the sodium salt of 4-nitrotoluene-2-sulfonic acid has become a dark green suspension, is now stirred for a further 5 hours at 0° to 5° C., whilst passing in dry air at a rate of 5 l/hour.

The green colour already disappears after about 3 hours and the reaction mixture changes to a yellow suspension as a result of partial precipitation of the reaction product formed and, after a further 2 hours, this suspension is neutralised with 108 ml of concentrated hydrochloric acid/water (1:1) at 0° to 5° C., the solvents are removed in vacuo and the residue is taken up in 200 ml of water. The reaction product is salted out with 200 ml of brine and the product which has precipitated is filtered off with suction, washed with 100 ml of sodium chloride solution/water (2:1) and dried to constant weight. 55 g of disodium 4,4'-dinitrostilbene-2,2'-disulfonate, of the formula

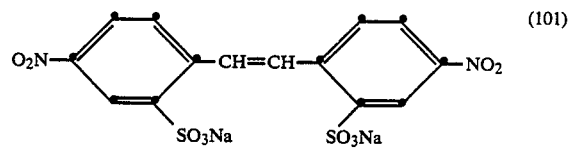

(101)

are obtained in the form of a yellow crystalline powder which has a melting point above 300° C. and has a NaCl content of 16.2% and an active content (determined by UV spectrophotometry) of 94.8%. The yield of disodium 4,4'-dinitrostilbene-2,2'-disulfonate is 92.1% of theory.

Similar results are obtained using hexamethylphosphoric acid triamide, diethylformamide, diethylacetamide or dimethylacetamide in place of dimethylformamide.

EXAMPLE 2

Example 1 is repeated except that, after the addition of the dimethylformamide solution of sodium 4-nitrotoluene-2-sulfonate, the reaction mixture is stirred for only a further 3 hours instead of for a further 5 hours, at 0° to 5° C., whilst passing in dry air at a rate of 5 l/hour.

53.2 g of disodium 4,4'-dinitrostilbene-2,2'-disulfonate are obtained in the form of a yellow crystalline powder which has a melting point above 320° C. and has a NaCl content of 16.4% and an active content (determined by UV spectrophotometry) of 94%.

The yield of disodium 4,4'-dinitrostilbene-2,2'-disulfonate is 88.2% of theory.

EXAMPLE 3

Example 1 is repeated except that:

(a) In place of 108 g of a methanolic 30% sodium methylate solution, 72 g of this solution are used.

(b) In place of a stream of dry air at a rate of 5 l/hour, a stream of dry air at a rate of 8 l/hour is used.

(c) after adding the dimethylformamide solution of sodium 4-nitrotoluene-2-sulfonate, the reaction mixture is stirred for only a further 4 hours, instead of a further 5 hours, at 0° to 5° C., whilst passing in dry air at a rate of 8 l/hour.

51.5 g of disodium 4,4'-dinitrostilbene-2,2'-disulfonate are obtained in the form of a yellow crystalline powder which has a melting point above 340° C. and has a NaCl content of 12.1% and an active content (determined by UV spectrophotometry) of 86.6%. The yield of disodium 4,4'-dinitrostilbene-2,2'-disulfonate is 82.7% of theory.

EXAMPLE 4

Example 1 is repeated, except that:

(a) In place of 50 ml of dimethylformamide, 100 ml of dimethylformamide are cooled to 0° C.

(b) In place of 108 g of a methanolic 30% sodium methylate solution, 72 g of this solution are used.

(c) In place of a stream of dry air at a rate of 5 l/hour, a stream of dry air at a rate of 8 l/hour is used.

(d) After adding the dimethylformamide solution of sodium 4-nitrotoluene-2-sulfonate, the reaction mixture is stirred for only a further 4 hours, instead of a further 5 hours, at 0° to 5° C., whilst passing in dry air at a rate of 8 l/hour.

46 g of disodium 4,4'-dinitrostilbene-2,2'-disulfonate are obtained in the form of a yellow crystalline powder which has a melting point above 340° C. and has a NaCl content of 11.1% and an active content (determined by UV spectrophotometry) of 98.2%. The yield of disodium 4,4'-dinitrostilbene-2,2'-disulfonate is 84.7% of theory.

EXAMPLE 5

Example 1 is repeated, except that:
(a) In place of 50 ml of dimethylformamide, 100 ml of dimethylformamide are cooled to 0° C.
(b) In place of 108 g of a methanolic 30% sodium methylate solution, 36 g of this solution are used.
(c) In place of a stream of dry air at a rate of 5 l/hour, a stream of dry air at a rate of 8 l/hour is used.
(d) After adding the dimethylformamide solution of sodium 4-nitrotoluene-2-sulfonate, the reaction mixture is stirred for a further 6 hours, instead of a further 5 hours, at 0° to 5° C., whilst passing in dry air at a rate of 8 l/hour.

35 g of disodium 4,4'-dinitrostilbene-2,2'-disulfonate are obtained in the form of a yellow crystalline powder which has a melting point above 340° C. and has a NaCl content of 13.8% and an active content (determined by UV spectrophotometry) of 96.7%. The yield of disodium 4,4'-dinitrostilbene-2,2'-disulfonate is 61.6% of theory.

EXAMPLE 6

27.8 g of powdered sodium methylate (97% pure) are taken up in 190 ml of dimethylformamide. 1 g of manganese sulfate monohydrate and 7 g of benzyl-tri-n-butylammonium bromide are added to the resulting suspension and the mixture is cooled to 0° C. The suspension is then saturated with air, at 0° to 5° C., with stirring, by passing in a stream of dry air for 15 minutes at a rate of 10 l/hour under a pressure (in the reaction flask) of 55 mm Hg, through a frit which dips into the suspension.

A solution of 48 g of sodium 4-nitrotoluene-2-sulfonate in 100 ml of dimethylformamide is now added dropwise in the course of two hours to this suspension, at 0° to 5° C., with stirring, whilst continuing to pass in the stream of dry air at a rate of 10 l/hour under a pressure (in the reaction flask) of 55 mm Hg, through the frit which dips into the suspension. The reaction mixture, which during the addition of the sodium salt of 4-nitrotoluene-2-sulfonic acid has become a dark green suspension, is now stirred for a further 6 hours at 0° to 5° C. whilst passing in dry air at a rate of 10 l/hour, under a pressure (in the reaction flask) of 55 mm Hg.

The dark brown reaction mixture is now neutralised at 0° to 5° C. with a solution of 45 ml of concentrated hydrochloric acid in 90 ml of water and freed from dimethylformamide in vacuo, and the residue is taken up in 150 ml of water. The reaction product is filtered off with suction at room temperature, washed with 50 ml of a 7.5% NaCl solution and dried to constant weight. 47.07 g of disodium 4,4'-dinitrostilbene-2,2'-disulfonate are obtained in the form of a yellow crystalline powder which has a melting point above 320° C. and has a NaCl content of 1.8%, a $H_2O$ content of 1.6% and an active content (determined by UV spectrophotometry) of 45.7%. The yield of disodium 4,4'-dinitrostilbene-2,2'-disulfonate is 43.7% of theory.

EXAMPLE 7

37.5 g of potassium hydroxide powder (90% pure) are dissolved in 100 ml of hot methanol. The resulting clear solution is cooled to 10° C., 1 g of manganese sulfate monohydrate is added and the mixture is diluted with 100 ml of dimethylformamide, whereupon the potassium hydroxide partially precipitates as a fine suspension. The reaction mixture is now cooled to 0° to 5° C. and at the same time is saturated with air by passing in a stream of dry air for 15 minutes at a rate of 8 l/hour, through a frit which dips into the solution. This 8 l/hour stream of air is kept constant throughout the entire oxidation.

A solution of 48 g of sodium 4-nitrotoluene-2-sulfonate in 100 ml of dimethylformamide is now added dropwise in the course of two hours, at 0° to 5° C., to the resulting thick slurry, with stirring, and the reaction mixture immediately becomes dark green in colour. The reaction mixture is then stirred for a further 6 hours at 0° to 5° C. and the reaction product separates out as an even thicker precipitate, the dark green colour slowly disappearing; the dark green colour has completely disappeared after about 4 hours. The stream of air is now discontinued and the dark yellow, crystalline reaction slurry which has formed is neutralised at 0° to 5° C. with a solution of 52 ml of concentrated hydrochloric acid in 90 ml of water. The pale yellow crystalline suspension is freed from solvents in vacuo, the residue is taken up in 200 ml of water and the product is salted out with 200 ml of a saturated solution of potassium chloride and filtered off with suction, washed with 100 ml of a saturated potassium chloride/water (2:1) solution and dried to constant weight.

50.01 g of dipotassium 4,4'-dinitrostilbene-2,2'-disulfonate are obtained in the form of a yellow crystalline powder which has a melting point above 320° C. and has a KCl content of 4.1% and an active content (determined by UV spectrophotometry) of 69.4%. The yield of dipotassium 4,4'-dinitrostilbene-2,2'-disulfonate is 67% of theory.

Similar results are obtained using diethylformamide, diethylacetamide or hexamethylphosphoric acid triamide in place of dimethylformamide.

EXAMPLE 8

24.5 g of sodium hydroxide powder (98% pure) are dissolved in 90 ml of hot methanol. The resulting virtually clear solution is cooled to 10° C., 1 g of manganese sulfate monohydrate is added and the mixture is diluted with 100 ml of dimethylformamide, whereupon the sodium hydroxide partially precipitates as a fine suspension. The reaction mixture is now cooled to 0° to 5° C. and at the same time is saturated with air by passing in a stream of dry air for 15 minutes at a rate of 8 l/hour, through a frit which dips into the solution. This 8 l/hour stream of air is then kept constant throughout the entire oxidation.

A solution of 48 g of sodium 4-nitrotoluene-2-sulfonate in 100 ml of dimethylformamide is now added dropwise in the course of two hours, at 0° to 5° C., to the resulting thick slurry, with stirring, and the reaction mixture immediately becomes dark green in colour. The reaction mixture is now stirred for a further 6 hours at 0° to 5° C. and the reaction product separates out as an ever thicker precipitate, the dark green colour slowly disappearing; the dark green colour has completely disappeared after about 3 hours.

The stream of air is now discontinued and the dark yellow, crystalline reaction slurry which has formed is neutralised at 0° to 5° C. with 104 ml of concentrated hydrochloric acid/water (1:1). The resulting pale yellow crystalline suspension is freed from solvents in vacuo and the residue is taken up in 200 ml of water.

The reaction product is salted out with 200 ml of sodium chloride solution and filtered off with suction, washed with 100 ml of sodium chloride solution/water (2:1) and dried to constant weight. 50.2 g of disodium 4,4'-dinitrostilbene-2,2'-disulfonate are obtained in the form of a pale yellow crystalline powder which has a melting point above 320° C. and has a NaCl content of 9.3% and an active content (determined by UV spectrophotometry) of 99.2%. The yield of disodium 4,4'-dinitrostilbene-2,2'-disulfonate is 95.2% of theory.

The IR spectrum of this product is identical to the IR spectrum of an analytically pure sample of disodium 4,4'-dinitrostilbene-2,2'-disulfonate, the one spectrum superimposing the other.

Similar results are obtained using hexamethylphosphoric acid triamide, diethylformamide or diethylacetamide in place of dimethylformamide.

EXAMPLE 9

Example 8 is repeated, except that:

(a) The sodium hydroxide powder is dissolved in 100 ml of hot methanol in place of 90 ml of hot methanol.

(b) After adding the dimethylformamide solution of sodium 4-nitrotoluene-2-sulfonate, the reaction mixture is stirred for only a further 4 hours instead of a further 6 hours at 0° to 5° C. whilst passing in dry air at a rate of 8 l/hour.

50.1 g of disodium 4,4'-dinitrostilbene-2,2'-disulfonate are obtained in the form of a pale yellow crystalline powder which has a melting point above 320° C. and has a NaCl content of 11.1% and an active content (determined by UV spectrophotometry) of 99.0%. The yield of disodium 4,4'-dinitrostilbene-2,2'-disulfonate is 92.9% of theory.

EXAMPLE 10

Example 8 is repeated, except that:

(a) 32 g of sodium hydroxide powder are used in place of 24.5 g of sodium hydroxide powder.

(b) The oxidation is carried out at 20° to 25° C. instead of at 0° to 5° C.

48.0 g of disodium 4,4'-dinitrostilbene-2,2'-disulfonate are obtained in the form of a dark yellow crystalline powder which has a melting point above 340° C. and has a NaCl content of 20.9% and an active content (determined by UV spectrophotometry) of 89.4%. The yield of disodium 4,4'-dinitrostilbene-2,2'-disulfonate is 71.6% of theory.

EXAMPLE 11

Example 8 is repeated, except that:

(a) 16 g of sodium hydroxide powder are used in place of 24.5 g of sodium hydroxide powder.

(b) The sodium hydroxide powder is dissolved in only 50 ml of hot methanol instead of in 90 ml.

(c) The sodium 4-nitrotoluene-2-sulfonate is dissolved in 150 ml of dimethylformamide instead of in 100 ml.

48.0 g of disodium 4,4'-dinitrostilbene-2,2'-disulfonate are obtained in the form of a pale yellow crystalline powder which has a melting point above 320° C. and has a NaCl content of 9.3% and an active content (determined by UV spectrophotometry) of 98.0%. The yield of disodium 4,4'-dinitrostilbene-2,2'-disulfonate is 90.1% of theory.

EXAMPLE 12

Example 8 is repeated, except that:

(a) 12.2 g of sodium hydroxide powder are used in place of 24.5 g of sodium hydroxide powder.

(b) The sodium hydroxide powder is dissolved in only 50 ml of hot methanol instead of in 90 ml.

(c) The reaction mixture is diluted with 140 ml of dimethylformamide instead of with 100 ml.

(d) The dimethylformamide solution of sodium 4-nitrotoluene-2-sulfonate is added dropwise in the course of one hour instead of in the course of two hours and the reaction mixture is then stirred for a further 7 hours instead of a further 6 hours.

44.5 g of disodium 4,4'-dinitrostilbene-2,2'-disulfonate are obtained in the form of a yellow crystalline powder which has a melting point above 320° C. and has a NaCl content of 40.6% and an active content (determined by UV spectrophotometry) of 99.7%. The yield of disodium 4,4'-dinitrostilbene-2,2'-disulfonate is 83.6% of theory.

EXAMPLE 13

Example 8 is repeated, except that:

(a) The sodium hydroxide powder is dissolved in 100 ml of hot methanol instead of in 90 ml.

(b) The oxidation is carried out without a catalyst.

42.04 g of disodium 4,4'-dinitrostilbene-2,2'-disulfonate are obtained in the form of a yellow crystalline powder which has a melting point above 320° C. and has a NaCl content of 10.2% and an active content (determined by UV spectrophotometry) of 98.5%. The yield of disodium 4,4'-dinitrostilbene-2,2'-disulfonate is 78.5% of theory.

EXAMPLE 14

Example 8 is repeated except that instead of 1 g of manganese sulfate monohydrate, 0.5 g of the catalyst is used. 50.63 g of disodium 4,4'-dinitrostilbene-2,2'-disulfonate are obtained in the form of a yellow crystalline powder which has a melting point above 320° C. and has a NaCl content of 11.7% and an active content (determined by UV spectrophotometry) of 96.9%. The yield of disodium 4,4'-dinitrostilbene-2,2'-disulfonate is 91.4% of theory.

EXAMPLE 15

Example 8 is repeated, except that:

(a) 8.2 g of sodium hydroxide powder are used in place of 24.5 g of sodium hydroxide powder.

(b) The sodium hydroxide powder is dissolved in only 50 ml of hot methanol instead of in 90 ml.

(c) The catalyst used is 1 g of manganese sulfate monohydrate plus 1 g of lead-II acetate trihydrate, instead of only 1 g of manganese sulfate monohydrate.

48.28 of disodium 4,4'-dinitrostilbene-2,2'-disulfonate are obtained in the form of a yellow crystalline powder which has a melting point above 300° C. and has a NaCl content of 12.3% and an active content (determined by UV spectrophotometry) of 99.3%. The yield of disodium 4,4'-dinitrostilbene-2,2'-disulfonate is 88.7% of theory.

EXAMPLE 16

Example 8 is repeated, except that 1 g of manganese-II nitrate tetrahydrate is used as the catalyst, in place of 1 g of manganese sulfate monohydrate.

47.75 g of disodium 4,4'-dinitrostilbene-2,2'-disulfonate are obtained in the form of a yellow crystalline powder which has a melting point above 300° C. and has a NaCl content of 7.3% and an active content (determined by UV spectrophotometry) of 97.4%. The yield of disodium 4,4'-dinitrostilbene-2,2'-disulfonate is 91.0% of theory.

Similar results arre obtained when Example 8 is repeated using manganese dioxide, manganese-II perchlorate hexahydrate, manganese-III acetate monohydrate, manganese-II acetylacetonate, manganese-II carbonate, manganese-II bromide tetrahydrate, manganese-II chloride tetrahydrate, nickel sulfate hexahydrate, nickel-II acetate tetrahydrate, nickel-II bromide trihydrate, nickel phthalocyanine, cobalt-II sulfate heptahydrate, cobalt-II acetate tetrahydrate or the like as the catalyst, in place of manganese sulfate monohydrate.

EXAMPLE 17

20.4 g of sodium hydroxide granules (98% pure) are dissolved in 90 ml of hot methanol. The resulting virtually clear solution is cooled to 10° C., 1 g of manganese sulfate monohydrate is added and the mixture is diluted with 100 ml of dimethylformamide, whereupon the sodium hydroxide partially precipitates as a fine suspension. The reaction mixture is now cooled to 0° to 5° C. and at the same time is saturated with air by passing in a stream of air for 15 minutes at a rate of 10 l/hour, under an elevated pressure (in the reaction flask) of 55 mm Hg, through a frit which dips into the solution. This 10 l/hour stream of air and the excess air pressure in the reaction flask of 55 mm Hg are kept constant throughout the entire oxidation.

A solution of 48 g of sodium 4-nitrotoluene-2-sulfonate in 100 ml of dimethylformamide is now added dropwise in the course of one hour, at 0° to 5° C., to the resulting thick slurry, with stirring, and the reaction mixture immediately becomes dark green in colour. The reaction mixture is now stirred for a further 2 hours and 45 minutes at 0° to 5° C. and the reaction product separates out as an ever thicker precipitate, the dark green colour slowly disappearing; the dark green colour has completely disappeared after about 2 hours and 15 minutes with vigorous stirring.

The stream of air is now discontinued and the dark yellow, crystalline reaction slurry which has formed is neutralised at 0° to 10° C. under normal pressure with a solution of 45 ml of concentrated hydrochloric acid in 90 ml of water. The resulting pale yellow crystalline suspension is concentrated to dryness in vacuo in a rotary evaporator.

The dry reaction mixture is taken up in 150 ml of water and stirred for a further 15 minutes in a rotary evaporator at 90° C., without applying a vacuum. The hot crystalline suspension is always allowed to cool to room temperature and is then filtered with suction and the product is washed with 50 ml of a 7.5% by weight sodium chloride solution and dried at 100° C. in vacuo to constant weight.

48.65 g of disodium 4,4'-dinitrostilbene-2,2'-disulfonate are obtained in the form of a pale yellow crystalline powder which has a melting point above 320° C. and has a NaCl content of 4.2%, a water content of 1.3% and an active content (determined by UV spectrophotometry) of 98.7%. The yield of disodium 4,4'-dinitrostilbene-2,2'-disulfonate is 95.6% of theory.

The IR spectrum of this product is identical to the IR spectrum of an analytically pure sample of disodium 4,4'-dinitrostilbene-2,2'-disulfonate, the one spectrum superimposing the other.

EXAMPLE 18

Example 17 is repeated except that the oxidation is carried out in a glass autoclave under an excess air pressure of one atmosphere, instead of under an excess air pressure of 55 mm Hg.

49.8 g of disodium 4,4'-dinitrostilbene-2,2'-disulfonate are obtained in the form of a pale yellow crystalline powder which has a melting point above 300° C. and has a NaCl content of 12.9%, a water content of 1.3% and an active content (determined by UV spectrophotometry) of 100%. The yield of disodium 4,4'-dinitrostilbene-2,2'-disulfonate is 90.3% of theory.

EXAMPLE 19

Example 17 is repeated, except that:
(a) The oxidation is carried out with oxygen instead of with air.
(b) The oxidation is carried out under atmospheric pressure instead of under elevated pressure.
(c) After adding the dimethylformamide solution of sodium 4-nitrotoluene-2-sulfonate, the reaction mixture is stirred for only a further one hour at 0° to 5° C., instead of for a further 2 hours and 45 minutes.

45.11 g of disodium 4,4'-dinitrostilbene-2,2'-disulfonate are obtained in the form of a yellow crystalline powder which has a melting point above 320° C. and has a NaCl content of 3.5%, a water content of 1.8% and an active content (determined by UV spectrophotometry) of 97.0%. The yield of disodium 4,4'-dinitrostilbene-2,2'-disulfonate is 87.4% of theory.

EXAMPLE 20

Example 17 is repeated, except that:
(a) The oxidation is carried out in the presence of 4.4 g of the crown ether 15-crown-5.
(b) The oxidation is carried out without methanol.

45.37 g of disodium 4,4'-dinitrostilbene-2,2'-disulfonate are obtained in the form of a pale yellow crystalline powder which has a melting point above 320° C. and has a NaCl content of 3.9%, a water content of 3.2% and an active content (determined by UV spectrophotometry) of 44.8%. The yield of disodium 4,4'-dinitrostilbene-2,2'-disulfonate is 39.8% of theory.

EXAMPLE 21

Example 17 is repeated except that, after the oxidation, the neutralised reaction mixture is first diluted with 150 ml of water and then heated to 60° C. The hot, clear reaction solution is added dropwise in the course of 20 minutes, at 90° C., to a suspension of 100 g of ground cast iron filings and 1 g of sodium acetate in 10 ml of 40% acetic acid, with vigorous stirring. The reaction mixture is now refluxed (90° C.) for two hours, with vigorous stirring, the pH is then adjusted to 9 with a solution of 35 g of sodium carbonate decahydrate in 50 ml of water and the resulting mixture is filtered hot, with suction. The clear filtrate is concentrated to dryness in vacuo in a rotary evaporator, the dry residue is taken up in 100 ml of water and, in a rotary evaporator, first 0.5 g of sodium dithionite and then 100 ml of sodium chloride solution are added at 90° C., without applying a vacuum, and the resulting mixture is stirred for a further 15 minutes. The hot crystalline suspension is allowed to cool to room temperature and is then filtered with suction and the product is washed with 50 ml of a sodium chloride solution/water (2:1) solution and dried at 100° C. in vacuo, to constant weight.

44.17 g of disodium 4,4'-diaminostilbene-2,2'-disulfonate are obtained in the form of a pale yellow, fine crystalline powder which has a melting point above 300° C. and has a NaCl content of 14.4%, a water content of 2.0% and an active content (determined by UV spectrophotometry) of 99.3%. The yield of disodium 4,4'-diaminostilbene-2,2'-disulfonate is 88.6% of theory, based on the sodium 4-nitrotoluene-2-sulfonate employed.

What I claim is:

1. A process for the preparation of 4,4'-dinitrostilbene-2,2'-disulfonic acid, or salt thereof, of the formula

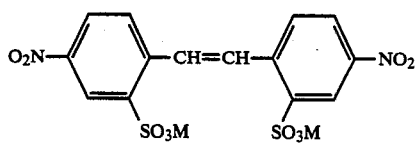

in which M is hydrogen or an alkali metal cation, which process comprises:
   a. oxygenating a reaction medium comprising:
      (i) a solvent selected from the group consisting of N-methylpyrrolidone; dimethylsulfoxide; sulfolane; acetonitrile; tetramethylurea; aprotic dipolar solvents of the formula

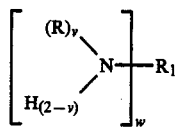

wherein R is a $C_1$-$C_4$-alkyl group, $R_1$ is a $C_1$-$C_4$-carboxylic acid or phosphoric acid radical, w is the basicity of the acid and the v's are 0, 1, or 2; and mixtures thereof, which solvent or solvent mixture is pure or combined with one or more $C_1$-$C_4$ alcohols;
      (ii) a catalytically-effective amount of a catalyst selected from the group consisting of salts, oxides, hydroxides and organic compounds of heavy metals; inorganic or organic bromine or iodine compounds; and phase transfer catalysts; and
      (iii) a catalytically effective amount of a strongly basic compound of aluminum, an alkali metal or an alkaline earth; or strongly basic ion exchanger; or mixture of any or all of these;
   b. dissolving 4-nitro-2-toluene sulfonic acid or alkali metal salt thereof in a solvent of step (a-i); and
   c. combining the solution of step (b) with the reaction medium of step (a) while continuously oxygenating the resulting mixture.

2. A process according to claim 1 wherein the catalyst is a salt, oxide, hydroxide or organic compound of manganese.

3. A process according to claim 1 wherein the aprotic dipolar solvent is dimethylformamide, diethylformamide, hexamethylphosphoric acid triamide, dimethylacetamide or diethylacetamide.

4. A process according to claim 3 wherein the solvent of step (a-l) is a mixture of dimethylformamide and methanol, diethylformamide and methanol, or dimethylformamide and diethylformamide and methanol.

5. A process according to claim 4 wherein said strongly basic compound is a hydroxide, amide, hydride, alcoholate, sulfide, or mixture thereof.

6. A process according to claim 5 wherein said strongly basic compound is a hydroxide, amide or alcoholate of potassium or sodium.

7. A process according to claim 1 wherein the strongly basic compound is used in an at least equivalent amount.

8. A process according to claim 1 wherein step (c) is conducted at a temperature of 0° C. to 25° C.

9. A process according to claim 1 wherein said catalyst is a phase transfer catalyst.

10. A process according to claim 1 wherein said oxygenating is effected with air, pure oxygen, or a mixture of oxygen with inert gas.

11. A process according to claim 1 wherein oxygenating is effected at supraatmospheric pressure.

12. A process for the preparation of 4,4'-dinitrostilbene-2,2'-disulfonic acid, or salt thereof, of the formula

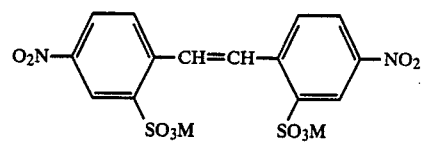

in which M is hydrogen or an alkali metal cation, which process comprises:
   a. oxygenating a reaction medium comprising:
      (i) a solvent selected from the group consisting of N-methylpyrrolidone; dimethylsulfoxide; sulfolane; acetonitrile; tetramethylurea; aprotic dipolar solvents of the formula

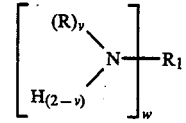

wherein R is a $C_1$-$C_4$-alkyl group, $R_1$ is a $C_1$-$C_4$-carboxylic acid or phosphoric acid radical, w is the basicity of the acid and the v's are 0, 1, or 2; and mixtures thereof, which solvent or solvent mixture is pure or combined with one or more $C_1$-$C_4$ alcohols;
      (ii) a catalytically effective amount of a manganese salt, oxide, hydroxide or organic compound; and
      (iii) a catalytically effective amount of a strongly basic compound of aluminum, an alkali metal or an alkaline earth; or strongly basic ion exchanger; or mixture of any or all of these;
   b. dissolving 4-nitro-2-toluene sulfonic acid or alkali metal salt thereof in a solvent of step (a-i); and
   c. adding the solution of step (b) to the reaction medium of step (a) while continuously oxygenating the resulting mixture.

13. A process according to claim 12 wherein said manganese salt is manganese (II) sulfate or nitrate and is used in an amount that is 0.1 to 15 percent by weight of the amount of 4-nitro-2-toluene sulfonic acid.

14. A process according to claim 13 wherein said aprotic dipolar solvent is dimethylformamide, hexamethylphosphoric acid triamide, dimethylformamide or diethylacetamide, dimethylacetamide or a mixture of any or all of these.

15. A process according to claim 13 wherein said strongly basic compound is a hydroxide, amide, hydride, alcoholate or sulfide of potassium or sodium, or mixture thereof and is used in an amount at least equivalent to the amount of 4-nitro-2-toluene sulfonic acid.

* * * * *